(12) United States Patent
Zhou et al.

(10) Patent No.: US 11,980,453 B2
(45) Date of Patent: May 14, 2024

(54) INTERFEROMETRIC TECHNIQUE FOR MEASURING CEREBRAL BLOOD FLOW USING INEXPENSIVE CMOS SENSORS

(71) Applicant: The Regents of the University of California, Oakland, CA (US)

(72) Inventors: Wenjun Zhou, Davis, CA (US); Oybek Kholiqov, Davis, CA (US); Vivek Jay Srinivasan, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 755 days.

(21) Appl. No.: 17/046,246

(22) PCT Filed: Apr. 15, 2019

(86) PCT No.: PCT/US2019/027546
§ 371 (c)(1),
(2) Date: Oct. 8, 2020

(87) PCT Pub. No.: WO2019/204231
PCT Pub. Date: Oct. 24, 2019

(65) Prior Publication Data
US 2021/0030284 A1    Feb. 4, 2021

Related U.S. Application Data

(60) Provisional application No. 62/658,442, filed on Apr. 16, 2018.

(51) Int. Cl.
*A61B 5/026* (2006.01)
*A61B 5/00* (2006.01)
(52) U.S. Cl.
CPC .......... *A61B 5/0261* (2013.01); *A61B 5/4064* (2013.01); *A61B 2562/0238* (2013.01); *A61B 2562/04* (2013.01)

(58) Field of Classification Search
CPC ............... A61B 5/0261; A61B 5/4064; A61B 2562/0238; A61B 2562/04
See application file for complete search history.

(56) References Cited

U.S. PATENT DOCUMENTS

| | | | | |
|---|---|---|---|---|
| 2003/0095263 | A1* | 5/2003 | Varshneya | A61B 5/4818 356/477 |
| 2010/0027857 | A1* | 2/2010 | Wang | A61B 5/0066 382/128 |
| 2012/0095354 | A1* | 4/2012 | Dunn | A61B 5/0261 600/504 |

OTHER PUBLICATIONS

Kholiqov et al., "Interferometric Near-Infrared Spectroscopy (NIRS): Performance Tradeoffs and Optimization", Optics Express, vol. 25, No. 23, pp. 28567-28588, Nov. 13, 2017.

(Continued)

*Primary Examiner* — Eric F Winakur
*Assistant Examiner* — Abid A Mustansir
(74) *Attorney, Agent, or Firm* — Park, Vaughan, Fleming & Dowler LLP (57) ABSTRACT

The disclosed embodiments provide a system that non-invasively analyzes blood flow in a sample of living tissue. During operation, the system obtains light from a temporally coherent source, and splits the obtained light between a reference path and a sample path. Next, the system multiply scatters light from the sample path by passing the light through the sample. The system then recombines light from the reference path and the multiply scattered light from the sample path. Next, the system uses a sensor array to detect an interference pattern resulting from the recombination. Finally, the system analyzes signals from the sensor array to determine a blood flow in the sample.

31 Claims, 5 Drawing Sheets

(56) References Cited

OTHER PUBLICATIONS

Dietsche et al., "Fiber-Based Multispeckle Detection for Time-Resolved Diffusing-Wave Spectroscopy: Characterization and Application to Blood Flow Detection in Deep Tissue", Applied Optics, vol. 46, No. 35, pp. 8506-8514, Dec. 7, 2007.
Dragojevic et al., "High-Speed Multi-Exposure Laser Speckle Contrast imaging with a Single-Photon Counting Camera", Biomedical Optics Express, vol. 6, No. 8, pp. 2865-2876, Jul. 14, 2015.
Kazmi et al., "Evaluating Multi-Exposure Speckle Imaging Estimates of Absolute Autocorrelation Times", Optics Letters, vol. 40, No. 15, pp. 3643-3646, Jul. 30, 2015.

* cited by examiner

INTERFEROMETRIC TECHNIQUE FOR MEASURING CEREBRAL BLOOD FLOW USING INEXPENSIVE CMOS SENSORS

RELATED APPLICATION

This application claims priority under 35 U.S.C. § 119 to U.S. Provisional Application No. 62/658,442, entitled "Interferometric Technique for Assessing Coherent Fluctuations of Diffuse Light," by inventors Vivek Srinivasan, Wenjun Zhou and Oybek Kholiqov, filed on 16 Apr. 2018, the contents of which are incorporated herein by reference.

GOVERNMENT LICENSE RIGHTS

This invention was made with U.S. government support under grant number R21 NS10504301 awarded by the National Institutes of Health (NIH). The U.S. government has certain rights in the invention.

BACKGROUND

Field

The disclosed embodiments generally relate to non-invasive techniques for measuring blood flow. More specifically, the disclosed embodiments relate to a non-invasive interferometric technique for measuring cerebral blood flow using inexpensive complementary metal-oxide-semiconductor (CMOS) sensors.

Related Art

Steady cerebral blood flow (CBF) is required for normal brain function. However, continuous monitoring of CBF in humans in natural environments is currently impractical. Researchers have investigated a number of non-invasive techniques that make use of the dynamics of scattered coherent light to non-invasively provide information about blood flow. For example, researchers have investigated diffuse correlation spectroscopy (DCS), which uses the temporal intensity fluctuations of light scattered multiple times from moving red blood cells to determine cerebral blood flow. (See Boas, D. A. & Yodh, A. G. Spatially varying dynamical properties of turbid media probed with diffusing temporal light correlation. *J Opt Soc Am A* 14, 192-215, doi:Doi 10.1364/Josaa.14.000192, 1997.)

Unfortunately, DCS presently relies on photon-counting technology, which costs several thousand dollars per detector, and is susceptible to ambient light noise. This means photon-counting detectors require preventative measures (i.e., turning off the lights) to avoid noise during DCS measurements. This sensitivity of DCS to ambient light limits the ability to perform CBF monitoring in natural conditions. Moreover, because DCS measures light fluctuations, detection systems must be single-mode or few-mode, which limits the photon count rates that DCS can measure. Because of this limitation, DCS detectors are usually placed less than 3 cm away from a corresponding DCS source, where re-emitted light levels are higher. Shorter source detector separations result in lower sensitivity to deep tissues.

To increase photon count rates, a technique, which uses "brute-force parallelization" with multiple avalanche photodiodes and dedicated single mode fiber collectors, has also been explored. However, high detector cost makes parallelization beyond a handful of detectors prohibitively expensive. (See Dietsche, G. et al. Fiber-based multispeckle detection for time-resolved diffusing-wave spectroscopy: characterization and application to blood flow detection in deep tissue. *Appl Opt* 46, 8506-8514, 2007.) Thus, the limited photon counts provided by DCS present a significant obstacle to achieving CBF monitoring with good brain sensitivity, high coverage, and high signal-to-noise ratio.

Hence, what is needed is a practical and effective non-invasive technique for measuring cerebral blood flow, which does not suffer from the above-described limitations of existing techniques.

SUMMARY

The disclosed embodiments provide a system that non-invasively analyzes blood flow in a sample of living tissue. During operation, the system obtains light from a temporally coherent source, and splits the obtained light between a reference path and a sample path. Next, the system multiply scatters light from the sample path by passing the light through the sample. The system then recombines light from the reference path and the multiply scattered light from the sample path. Next, the system uses a sensor array to detect an interference pattern resulting from the recombination. Finally, the system analyzes signals from the sensor array to determine a blood flow in the sample.

In some embodiments, the sample path comprises a multi-mode fiber (MMF) after the sample.

In some embodiments, the sample path comprises a bundle of single-mode fibers (SMFs) after the sample.

In some embodiments, while analyzing the signals from the sensor array, the system uses a multi-exposure heterodyne technique to determine the blood flow in the sample.

In some embodiments, while analyzing the signals from the sensor array, the system assesses dynamics of blood flow in the sample by analyzing fluctuations in an interference time course.

In some embodiments, the system assesses the dynamics of the blood flow in the sample by varying an exposure time of the sensor array and analyzing resulting changes in an interference pattern as a function of exposure time at two or more distinct exposure times.

In some embodiments, while analyzing the signals from the sensor array, the system first performs a rolling mean subtraction operation on the signals to filter out a reference term. Next, the system performs a binning operation that sums up signals from groups of two or more spatially adjacent pixels. The system then performs an autocorrelation operation on the signals of the binned pixels to determine how fast the signals are changing. Next, the system uses a light scattering model and a fitting procedure to fit a decay rate for the summed autocorrelation. The system then determines from the decay rate a blood flow index (BFI) for the sample. Finally, the system displays a time course for the BFI.

In some embodiments, the system may determine an amplitude of the summed autocorrelation (or the sum of the squared heterodyne signals of the binned pixels). This amplitude is proportional to the number of photons collected from the sample, and may be displayed as a time course, or further analyzed, as is well known to a person of ordinary skill in the art of continuous wave near-infrared spectroscopy.

In some embodiments, the system varies a wavelength of the temporally coherent source over time.

In some embodiments, light travelling through the reference path and the sample path is separated and recombined using a beam splitter and/or a fiber coupler.

In some embodiments, the sample and reference paths include optics before or after the recombining beam splitter (or fiber coupler) to increase a number of speckles.

In some embodiments, a reference count level for light from the reference path is more than ten times greater than a sample count level for light from the sample path.

In some embodiments, the reference count level for light from the reference path is more than 20 million counts per second for each element in the detector array.

In some embodiments, the sensor array comprises a complementary metal-oxide-silicon (CMOS) array detector.

In some embodiments, the tissue comprises human brain tissue and the blood flow comprises cerebral blood flow.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

DISCUSSION

Fluctuations of scattered light can non-invasively probe the microscopic motion of scatterers in turbid media such as colloids, foams, gels, and biological tissue. For example, a technique known as "diffusing wave spectroscopy" (DWS) uses intensity fluctuations of multiply scattered coherent light to infer the dynamics of a turbid medium or sample. (See D. J. Pine, D. A. Weitz, P. M. Chaikin, and E. Herbolzheimer, "Diffusing wave spectroscopy," Phys. Rev. Lett. 60, 1134-1137, 1988.) When informed by a light transport model that incorporates medium optical properties, illumination, and collection geometry, DWS can quantify particle dynamics. When DWS is applied to quantify blood flow in biological tissue by modeling transport with the correlation diffusion equation solution for a semi-infinite turbid medium, the term "diffuse correlation spectroscopy" (DCS) is used. (See T. Durduran, and A. G. Yodh, "Diffuse correlation spectroscopy for noninvasive, micro-vascular cerebral blood flow measurement," NeuroImage 85, 51-63, 2014.) Compared to singly scattered light dynamics, multiply scattered light dynamics can interrogate shorter time scales of motion, and probe deeper into turbid media such as the human head. However, the available surface flux of diffuse light, which experiences many scattering events and penetrates deeply, is weak. DWS and DCS are both homodyne techniques, because they measure the intensity fluctuations formed by self-interference of changing light fields from various scattered sample paths. Because single-speckle or few-speckle collection is needed to measure these fluctuations, and light fluxes are low, single photon counting is required.

Heterodyne optical methods interfere a strong reference light field with the weak scattered sample field(s) to boost signals. Optical coherence tomography (OCT) is a widespread optical heterodyne technique that forms images with quasi-ballistic back-reflected light, usually with a single-mode fiber (SMF) collector. However, heterodyne interferometry is rarely applied to diffuse optical measurements such as DWS. Heterodyne interferometry with a single detector has been applied to study the transition from ballistic to diffusive transport in suspensions. However, to date, deep tissue blood flow experiments have exclusively used homodyne DCS. The use of SMF or few-mode fiber (FMF) collectors in homodyne DCS limits achievable photon count rates at large source-detector (S-D) separations, making deep tissue, high-speed measurements challenging.

While time-of-flight-resolved methods enable deep tissue measurements at short S-D separations, their speed remains limited by the collection fiber throughput. While MMFs improve throughput, MMFs are typically not used for collection in DWS and DCS.

Conventional wisdom states that heterodyne interferometry should not be performed with MMF collection. Indeed, in heterodyne interferometry, multiple sample and reference modes interfering on a single detector reduce the mutual coherence, which negates the higher MMF throughput. Also, with coherent superposition of modes, one detector cannot measure more than one speckle. For these reasons, while MMFs are used occasionally in interferometers with single detectors, these systems cannot effectively utilize the high MMF throughput. Similarly, conventional wisdom states that homodyne interferometry (such as DCS) should not be performed with MMF collection. In homodyne interferometry, multiple modes on a single detector reduce the speckle contrast (coherence factor), which hinders measurements of intensity dynamics. Thus, in the DWS/DCS literature, bundles of SMF or FMF collector(s) with dedicated single-photon-counting detector(s) are typically employed to achieve high-throughput, multispeckle detection needed for high-speed, deep tissue sensing. However, avalanche photodiode arrays and associated electronics are expensive, limiting the number of possible channels. Moreover, multispeckle systems with CCD cameras cannot currently capture rapid temporal dynamics, and camera noise may further degrade the performance of homodyne techniques.

To address these issues, we have developed a heterodyne technique called "interferometric DWS" (iDWS) which, contrary to conventional wisdom, uses a MMF collector or a bundle of SMFs, along with a detector array to parallelize measurements, and thereby facilitate deep tissue measurements without single-photon-counting detectors. We show that an appropriate detector array can realize the benefits of MMF light throughput and multispeckle detection, while preserving coherence. Based on these results, we have developed a system that uses a CMOS line-scan camera as a detector. Though the camera is not scientific grade, heterodyne gain enables nearly shot noise limited performance.

Our preliminary results show that, via interferometry, a non-scientific grade CMOS sensor can be transformed into a massively parallel, low-cost detector array whose performance approaches that of many parallel photon-counting channels. Note that CMOS technology is widely used in cellular phones, web cameras, single lens reflex cameras, and sensors for autonomous driving vehicles. These existing economies of scale are continually driving advances in CMOS technology, which will further advance our invention in turn.

The iDWS technique improves both the performance and cost of CBF monitoring. This is achieved by replacing expensive photon-counting detectors used in DCS with a CMOS array. To render the CMOS pixels sensitive to weak light fields that probe CBF in the brain, we boost the weak optical field returning from the brain with a strong reference field through optical interferometry. With interferometry, we can achieve signal-to-noise ratios that are limited by fundamental photon noise, not CMOS sensor noise. We also use a multi-mode fiber (MMF) to improve light collection, as compared to single-mode or few-mode fibers used in conventional DCS, and individual pixels of the CMOS array quantify field fluctuations related to sample dynamics. Using this iDWS system, we can perform high-speed measurements of pulsatile blood flow in the human brain in vivo at a >3 cm S-D separation (>80 speckles, 0.1 s integration time).

iDWS System

Figure 1:
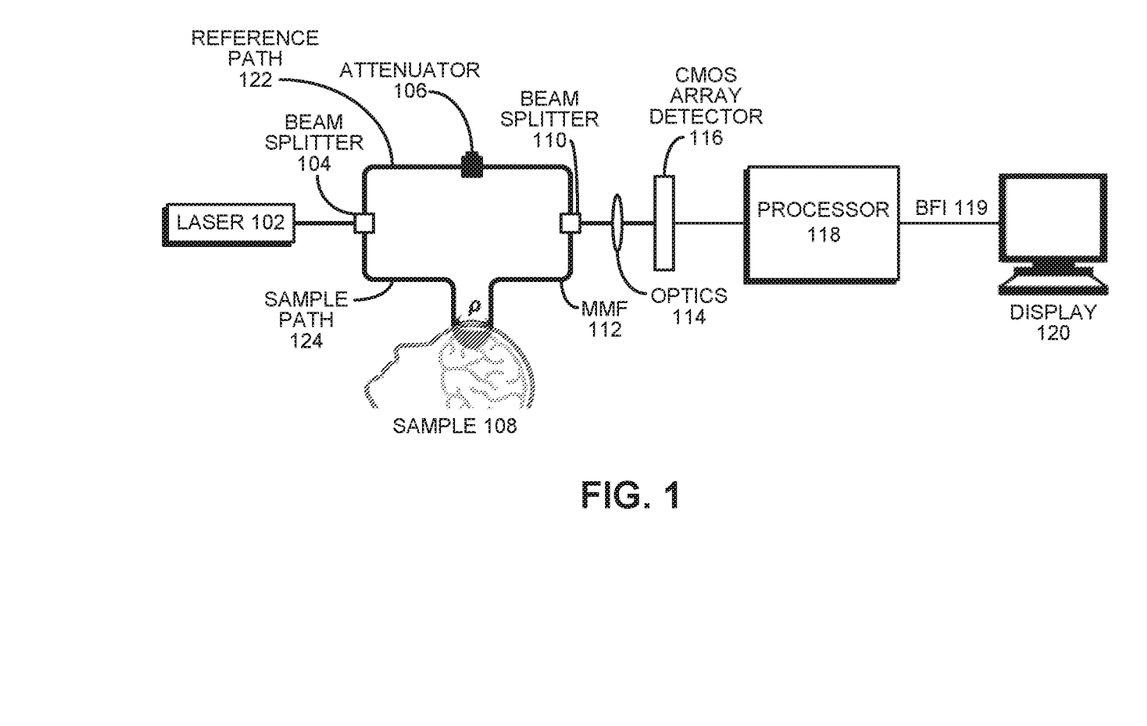
FIG. 1 presents a block diagram of an interferometric diffusing wave spectroscopy system with a multi-mode fiber collector in a sample arm and a CMOS sensor array to parallelize detection in accordance with the disclosed embodiments.

FIG. 1 illustrates a multi-mode interferometric multi-speckle detection system (i.e. multi-mode iDWS) for measuring coherent light scattering dynamics. This system is based on a Mach-Zehnder (M-Z) interferometer built from two fiber couplers. The light source is a laser 102, which can be implemented using an 852 nm DBR (distributed Bragg reflector) laser with <1 MHz line width and >180 mW output power, modulated by a 500 mA LC (laser controller, D2-105-500, Vescent Photonics) with a PS (power supply, D2-005, Vescent Photonics). Long coherence length light at 852 nm from laser 102 is split between a sample path 124 and reference path 122 of an M-Z interferometer by a beam splitter 104, which comprises a fused SMF-28 fiber coupler. This coupler supports the first 6 vectorial modes (HE11×2, TE01, HE21×2, and TM01) at 852 nm. In the reference path 122, the SMF-28 output fiber connects to a MMF coupler via an APC mating sleeve, with a variable attenuator 106 to avoid camera saturation. The splitting ratio of the MMF coupler is 95/5 (T/R). The core and cladding diameters of the step index MMF are 105 and 125 µm, respectively, and the numerical aperture (NA) is 0.15.

A collimated 50 mW sample beam with a spot size of 4 mm (below the ANSI maximum permissible exposure of 4 mW/mm$^2$) is used for irradiating a sample 108 (e.g. human brain tissue). Diffusively reflected light from the sample is collected by a MMF 112 at a distance p away (with a detection spot size of <1.5 mm), and is then combined with the reference light from reference path 122 in a fiber-optic beam splitter 110 (i.e., beam-splitter-based MMF coupler, FOBS-22P-1111-105/125-MMMM-850-95/5-35-3A3A3A3A-3-1NA=0.15, OZ Optics). The MMF coupler output is detected by a CMOS array detector 116 comprising a line-scan CMOS camera (spL4096-140 km, Basler) with a 333 kHz line rate for 512 horizontal pixels, vertical pixel binning, and 4-tap/12-bit data acquisition. An optics unit 114 comprising a set of cylindrical lenses projects the MMF output speckle pattern, with a diameter of 105 onto the 512 by 2 camera pixel array with dimensions of 5120 by 20 µm (10×10 µm pixels). In other embodiments, optics are placed before the beam splitter in the sample and reference paths to increase the speckle number.

Finally, the signals produced by CMOS array detector 116 are processed using a processor 118 to produce a BFI 119, which is displayed in the form of a time course on a display 120. These processing operations are described in more detail below with reference to the flow chart illustrated in FIG. 4.

Figure 2A:
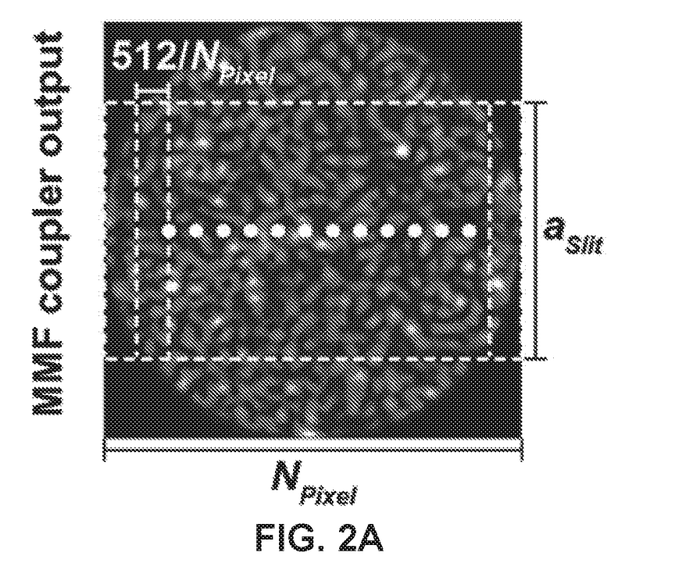
FIG. 2A illustrates an intensity pattern for a MMF output in accordance with the disclosed embodiments.

As shown in the simulation results presented in FIG. 2A, because a quasi-one-dimensional (1D) camera measures a two-dimensional (2D) interference pattern, each pixel detects the power over a vertical rectangular region of a speckle pattern. FIG. 2A illustrates an intensity pattern at the MMF coupler output, which is detected using a 512 pixel CMOS array. Note that the pixels are binned horizontally to form $N_{Pixel}$ binned pixels consisting of $512/N_{Pixel}$ pixels each, with fractional heights of $a_{Slit}$.

Figure 2B:
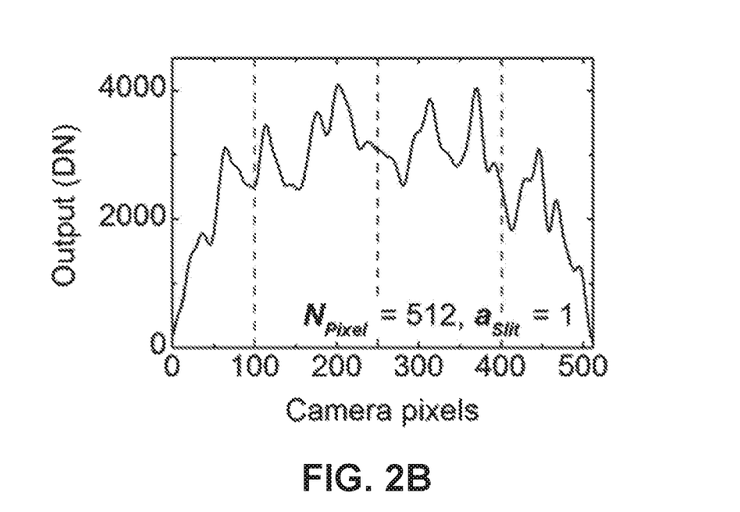
FIG. 2B illustrates instantaneous power measured by a pixel array in accordance with the disclosed embodiments.

A graph of instantaneous power is shown in FIG. 2B, with 512 pixels measuring the entire interference pattern (i.e. $N_{Pixel}$=512, $a_{Slit}$=1). Mean-subtracted power time courses yield heterodyne signals for each pixel. Thus, 512 pixels, in the case of no binning, yield 512 heterodyne signals to estimate 512 field autocorrelations that contain information about sample dynamics. Based on a theoretical analysis, we know that only an area-scan camera can possibly maximize the MCD and speckle number of multi-mode heterodyne signals. However, for in vivo monitoring of blood flow, a line-scan camera with a fast line rate (>100 kHz), manageable data volume, and low cost can be used for the multi-mode iDWS system. Due to the mismatch between the 2D multi-mode interference pattern and quasi-1D sensor array, an optimal signal-to-additive-noise ratio (SANR) and speckle number cannot be achieved from the heterodyne signals, $N_{AC}(t_d)$. Yet, relative to a single detector, sensor arrays improve achievable SANR and speckle number considerably.

Figure 2C:
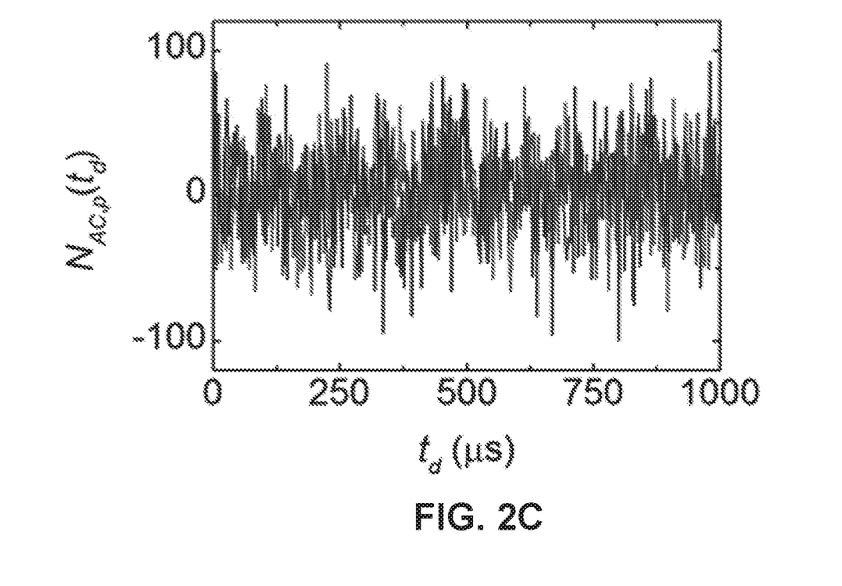
FIG. 2C illustrates segments of heterodyne signal time courses extracted from three pixels in accordance with the disclosed embodiments.
Figure 2D:
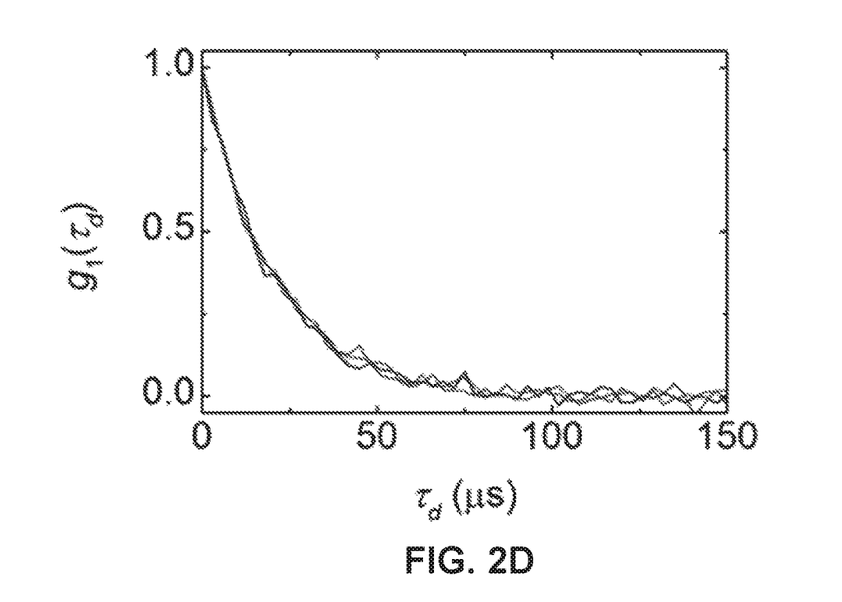
FIG. 2D illustrates normalized field autocorrelations calculated from full time courses for the three heterodyne signals illustrated in FIG. 2C in accordance with the disclosed embodiments.

FIG. 2C illustrates segments of heterodyne signal time courses (~1 ms) extracted from the three pixels marked by vertical dashed lines in FIG. 2B. Finally, FIG. 2D illustrates normalized field autocorrelations calculated from full time courses (~100 ms) of the three heterodyne signals in FIG. 2C.

Method of Operation

Figure 3:
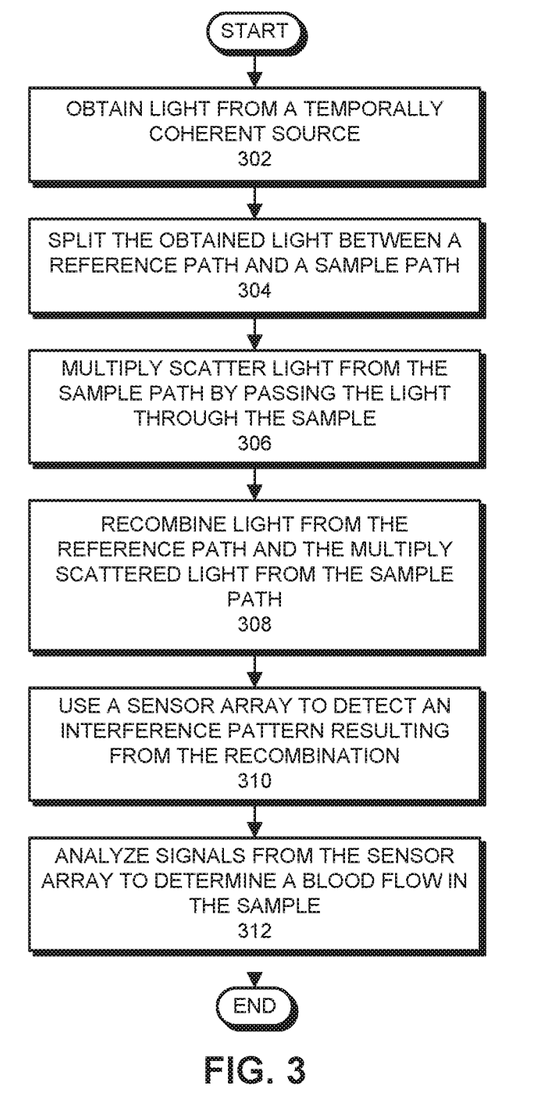
FIG. 3 presents a flow chart illustrating operations performed while non-invasively analyzing human tissue to determine a BFI in accordance with the disclosed embodiments.

FIG. 3 presents a flow chart illustrating operations performed while non-invasively analyzing human tissue to determine a BFI in accordance with the disclosed embodiments. The system first obtains light from a temporally coherent source (step 302), and splits the obtained light between a reference path and a sample path (step 304). Next, the system multiply scatters light from the sample path by passing the light through the sample (step 306). (When we say that the light is "multiply scattered," this indicates that photons that comprise the light have been subject to multiple scattering events while passing through the sample.) The system then recombines light from the reference path and the multiply scattered light from the sample path (step 308). Next, the system uses a sensor array to detect an interference pattern resulting from the recombination (step 310). Finally, the system analyzes signals from the sensor array to determine a blood flow in the sample (step 312).

Figure 4:
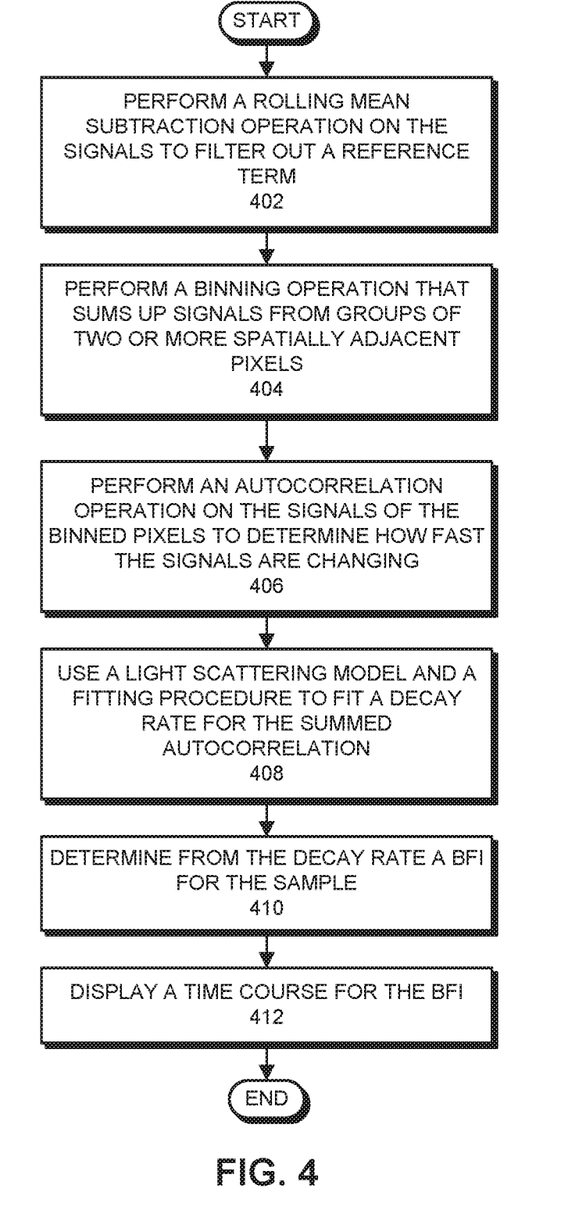
FIG. 4 presents a flow chart illustrating operations performed on signals gathered from a CMOS detector array to determine a BFI and display an associated time course in accordance with the disclosed embodiments.

FIG. 4 presents a flow chart illustrating operations performed on signals gathered from the CMOS detector array to determine a BFI and display an associated time course in accordance with the disclosed embodiments. The system first performs a rolling mean subtraction operation on the signals to filter out a reference term (step 402). Next, the system performs a binning operation that sums up signals from groups of two or more spatially adjacent pixels (step 404). The system then performs an autocorrelation operation on the signals of the binned pixels to determine how fast the signals are changing (step 406). Next, the system uses a light scattering model and a fitting procedure to fit a decay rate for the summed autocorrelation (step 408). The system then determines from the decay rate a blood flow index (BFI) for the sample (step 410). Finally, the system displays a time course for the BFI (step 412).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for non-invasively analyzing blood flow in a sample of living tissue, comprising:
    obtaining narrow-band light from a temporally coherent source;
    splitting the obtained narrow-band light between a reference path and a sample path;
    multiply scattering light from the sample path by passing the light through the sample;
    recombining light from the reference path and the multiply scattered light from the sample path;
    using a sensor array to detect an interference pattern resulting from the recombination; and
    analyzing signals from the sensor array to determine a blood flow in the sample.

2. The method of claim 1, wherein the sample path comprises a multi-mode fiber after the sample.

3. The method of claim 1, wherein the sample path comprises a bundle of single-mode fibers after the sample.

4. The method of claim 1, wherein analyzing the signals from the sensor array involves using a multi-exposure heterodyne technique to determine the blood flow in the sample.

5. The method of claim 1, wherein analyzing the signals from the sensor array involves assessing dynamics of blood flow in the sample by analyzing fluctuations in an interference time course.

6. The method of claim 5, wherein the dynamics of the blood flow in the sample are assessed by varying an exposure time of the sensor array and analyzing resulting changes in an interference pattern as a function of exposure time at two or more distinct exposure times.

7. The method of claim 1, wherein analyzing the signals from the sensor array involves:
    performing a rolling mean subtraction operation on the signals to filter out a reference term;
    performing a binning operation that sums up signals from groups of two or more spatially adjacent pixels;
    performing an autocorrelation operation on signals for each of the binned pixels to determine how fast the signals are changing; using a light scattering model and a fitting procedure to fit a decay rate for the summed autocorrelation;
    determining from the decay rate a blood flow index (BFI) for the sample; and
    displaying a time course for the BFI.

8. The method of claim 1, wherein analyzing the signals from the sensor array involves determining the sum of the squared heterodyne signals of the pixels.

9. The method of claim 1, wherein a wavelength of the temporally coherent source is varied over time.

10. The method of claim 1, wherein light travelling through the reference path and the sample path is separated and recombined using a beam splitter and/or a fiber coupler.

11. The method of claim 1, wherein the sample and reference paths include optics before or after the recombining beam splitter or fiber coupler to increase a number of speckles.

12. The method of claim 1, wherein a reference count level for light from the reference path is more than ten times greater than a sample count level for light from the sample path.

13. The method of claim 1, wherein the reference count level for light from the reference path is more than 20 million counts per second for each element in the detector array.

14. The method of claim 1, wherein the sensor array comprises a complementary metal-oxide-silicon (CMOS) array detector.

15. The method of claim 1, wherein the tissue comprises human brain tissue and the blood flow comprises cerebral blood flow.

16. A system that non-invasively analyzes blood flow in a sample of living tissue, comprising:
    a temporally coherent light source;
    a splitter, which splits narrow-band light from the temporally coherent light source between a reference path and a sample path;
    the reference path, which carries light from the splitter to a recombiner;
    the sample path, which passes light through the sample to produce multiply scattered light, and feeds the multiply scattered light into the recombiner;
    the recombiner, which recombines the light from the reference path and the multiply scattered light from the sample path;
    a sensor array, which detects an interference pattern resulting from the recombination; and
    an analysis mechanism, which analyzes signals from the sensor array to determine a blood flow in the sample.

17. The system of claim 16, wherein the sample path comprises a multi-mode fiber after the sample.

18. The system of claim 16, wherein the sample path comprises a bundle of single-mode fibers after the sample.

19. The system of claim 16, wherein while analyzing the signals from the sensor array, the analysis mechanism uses a multi-exposure heterodyne technique to determine the blood flow in the sample.

20. The system of claim 16, wherein while analyzing the signals from the sensor array, the analysis mechanism assesses dynamics of blood flow in the sample by analyzing fluctuations in an interference time course.

21. The system of claim 20, wherein the analysis mechanism analyzes dynamics of the blood flow in the sample by varying an exposure time of the sensor array and analyzing resulting changes in an interference pattern as a function of exposure time at two or more distinct exposure times.

22. The system of claim 16, wherein while analyzing the signals from the sensor array, the analysis mechanism:
    performs a rolling mean subtraction operation on the signals to filter out a reference term;
    performs a binning operation that sums up signals from groups of two or more spatially adjacent pixels;
    performs an autocorrelation operation on the signals of binned pixels to determine how fast the signals are changing; uses a light scattering model and a fitting procedure to fit a decay rate for the summed autocorrelation;
    determines from the decay rate a blood flow index (BFI) for the sample; and
    displays a time course for the BFI.

23. The system of claim 16, wherein while analyzing the signals from the sensor array, the analysis mechanism determines the sum of the squared heterodyne signals of the pixels.

24. The system of claim 16, wherein the temporally coherent light source includes an adjustment mechanism, which is used to vary a wavelength of the temporally coherent light source over time.

25. The system of claim 16, wherein the splitter and the recombiner are implemented using a beam splitter and/or a fiber coupler.

26. The system of claim 16, wherein the sample and reference paths include optics before or after the recombiner to increase a number of speckles.

27. The system of claim 16, wherein the recombiner is disposed to maximize a number of speckles detected by the sensor array.

28. The system of claim 16, wherein a reference count level for light from the reference path is more than ten times greater than a sample count level for light from the sample path.

29. The system of claim 16, wherein the reference count level for light from the reference path is more than 20 million counts per second for each element in the detector array.

30. The system of claim 16, wherein the sensor array comprises a complementary metal-oxide-silicon (CMOS) array detector.

31. The system of claim 16, wherein the tissue comprises human brain tissue and the blood flow comprises cerebral blood flow.

* * * * *